United States Patent [19]
Selmon et al.

[11] Patent Number: 5,968,064
[45] Date of Patent: *Oct. 19, 1999

[54] CATHETER SYSTEM FOR TREATING A VASCULAR OCCLUSION

[75] Inventors: Matthew R. Selmon, Woodside; Gerald Hansen, Newark; Charles Milo, Union City, all of Calif.

[73] Assignee: LuMend, Inc., Redwood City, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/775,264

[22] Filed: Feb. 28, 1997

[51] Int. Cl.⁶ .......................... A61B 17/00; A61M 25/00
[52] U.S. Cl. ...................... 606/189; 606/198; 604/96; 604/104
[58] Field of Search .................. 606/1, 159, 170, 606/171, 180, 198, 191; 604/22, 104, 105

[56] References Cited

U.S. PATENT DOCUMENTS

| | | |
|---|---|---|
| Re. 32,158 | 5/1986 | Vukovic . |
| 832,201 | 10/1906 | Kistler . |
| 1,127,948 | 2/1915 | Wappler . |
| 1,267,066 | 5/1918 | Flack . |
| 2,621,651 | 12/1952 | Wallace . |
| 3,640,270 | 2/1972 | Hoffman . |
| 3,667,474 | 6/1972 | Lapkin et al. . |
| 4,043,323 | 8/1977 | Komiya . |
| 4,355,643 | 10/1982 | Laughlin et al. . |
| 4,541,433 | 9/1985 | Baudino . |
| 4,572,186 | 2/1986 | Gould et al. . |
| 4,585,000 | 4/1986 | Hershenson . |
| 4,630,609 | 12/1986 | Chin . |
| 4,648,402 | 3/1987 | Santos . |
| 4,669,467 | 6/1987 | Willett et al. . |
| 4,681,110 | 7/1987 | Wiktor . |
| 4,698,057 | 10/1987 | Joishy . |
| 4,723,549 | 2/1988 | Wholey et al. . |
| 4,737,142 | 4/1988 | Heckele . |
| 4,787,388 | 11/1988 | Hofmann . |
| 4,794,928 | 1/1989 | Kletschka .................. 606/159 |
| 4,848,336 | 7/1989 | Fox et al. . |
| 4,862,874 | 9/1989 | Kellner . |
| 4,919,112 | 4/1990 | Siegmund . |
| 5,001,556 | 3/1991 | Nakamura et al. . |
| 5,011,488 | 4/1991 | Ginsburg . |
| 5,019,040 | 5/1991 | Itaoka et al. . |

(List continued on next page.)

FOREIGN PATENT DOCUMENTS

| | | |
|---|---|---|
| 0 377 269 A1 | 7/1990 | European Pat. Off. . |
| 0 521 595 A2 | 1/1993 | European Pat. Off. . |
| 1585065 | 1/1970 | France . |
| 2945237 A1 | 5/1981 | Germany . |
| 4429117 A1 | 2/1996 | Germany . |
| 0134398 | 1/1960 | Russian Federation ............... 606/198 |
| 134398 | 1/1960 | Russian Federation . |
| WO83/03188 | 9/1983 | WIPO . |
| Wo91/19528 | 12/1991 | WIPO . |
| WO92/08510 | 5/1992 | WIPO . |
| WO93/18818 | 9/1993 | WIPO . |
| WO95/19143 | 7/1995 | WIPO . |
| WO96/01590 | 1/1996 | WIPO . |
| WO96/11636 | 4/1996 | WIPO . |

Primary Examiner—Michael Buiz
Assistant Examiner—William W. Lewis
Attorney, Agent, or Firm—Wilson Sonsini Goodrich & Rosati

[57] ABSTRACT

Disclosed herein is a blunt end assembly including a catheter and a blunt end member. The blunt end member includes jaw sections which have a first closed position for locating the blunt end member at the site of the occlusion within the native lumen of the blood vessel and a second open position wherein the jaw sections are able to press against the interior walls of the lumen adjacent the occlusion. The assembly includes an actuation member for moving the jaw sections from the closed to the open positions repeatedly resulting in a fracturing of the occlusion. A guide wire may be thread through an internal opening in the catheter and the blunt end member and after fracturing, across the occlusion.

27 Claims, 3 Drawing Sheets

U.S. PATENT DOCUMENTS

| | | |
|---|---|---|
| 5,030,201 | 7/1991 | Palestrant . |
| 5,034,001 | 7/1991 | Garrison et al. . |
| 5,092,839 | 3/1992 | Kipperman . |
| 5,098,381 | 3/1992 | Schneider . |
| 5,099,850 | 3/1992 | Matsui et al. . |
| 5,100,425 | 3/1992 | Fischell et al. . |
| 5,102,390 | 4/1992 | Crittenden et al. . |
| 5,114,414 | 5/1992 | Buchbinder . |
| 5,179,961 | 1/1993 | Littleford et al. . |
| 5,180,368 | 1/1993 | Garrison . |
| 5,192,290 | 3/1993 | Hilal . |
| 5,193,546 | 3/1993 | Shaknovich . |
| 5,209,729 | 5/1993 | Hofmann et al. . |
| 5,211,654 | 5/1993 | Kaltenbach . |
| 5,217,484 | 6/1993 | Marks . |
| 5,263,959 | 11/1993 | Fischell . |
| 5,263,963 | 11/1993 | Garrison et al. . |
| 5,279,565 | 1/1994 | Klein et al. . |
| 5,282,817 | 2/1994 | Hoogeboom et al. . |
| 5,304,199 | 4/1994 | Myers . |
| 5,321,501 | 6/1994 | Swanson et al. . |
| 5,334,210 | 8/1994 | Gianturco . |
| 5,336,252 | 8/1994 | Cohen . |
| 5,350,377 | 9/1994 | Winston et al. . |
| 5,351,678 | 10/1994 | Clayton et al. . |
| 5,383,467 | 1/1995 | Auer et al. . |
| 5,409,453 | 4/1995 | Lundquist et al. . |
| 5,415,636 | 5/1995 | Forman . |
| 5,423,846 | 6/1995 | Fischell . |
| 5,439,000 | 8/1995 | Gunderson et al. . |
| 5,456,667 | 10/1995 | Ham et al. . |
| 5,459,570 | 10/1995 | Swanson et al. . |
| 5,484,412 | 1/1996 | Pierpont . |
| 5,486,170 | 1/1996 | Winston et al. . |
| 5,486,193 | 1/1996 | Bourne et al. . |
| 5,490,859 | 2/1996 | Mische et al. . |
| 5,499,995 | 3/1996 | Teirstein . |
| 5,501,694 | 3/1996 | Ressemann et al. . |
| 5,507,295 | 4/1996 | Skidmore . |
| 5,507,296 | 4/1996 | Bales et al. . |
| 5,511,559 | 4/1996 | Vance . |
| 5,522,819 | 6/1996 | Graves et al. . |
| 5,540,707 | 7/1996 | Ressemann et al. . |
| 5,573,531 | 11/1996 | Gregory . |
| 5,599,306 | 2/1997 | Klein et al. . |
| 5,618,300 | 4/1997 | Marin et al. . |
| 5,626,599 | 5/1997 | Bourne et al. . |
| 5,626,607 | 5/1997 | Malecki et al. . |
| 5,649,941 | 7/1997 | Lary . |
| 5,653,684 | 8/1997 | Laptewicz et al. . |
| 5,662,671 | 9/1997 | Barbut et al. . |
| 5,688,234 | 11/1997 | Frisbie ................................ 606/159 |
| 5,707,390 | 1/1998 | Bonutti . |
| 5,713,907 | 2/1998 | Hogendijk et al. ................ 606/198 |
| 5,800,450 | 9/1998 | Lary et al. . |
| 5,816,923 | 10/1998 | Milo et al. . |

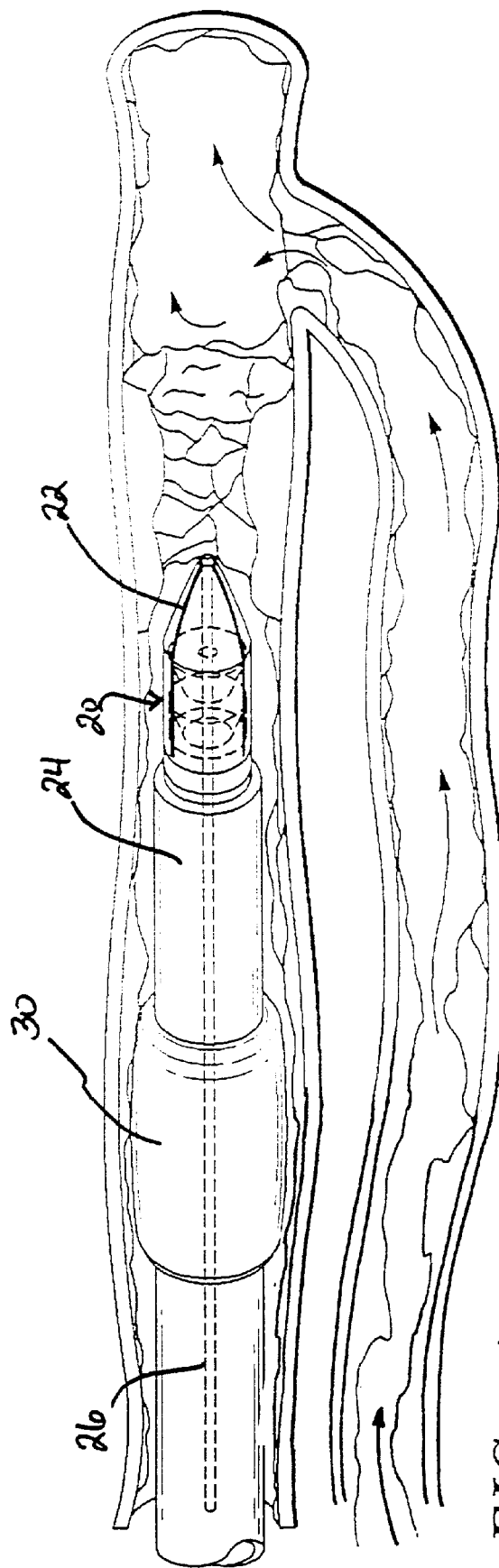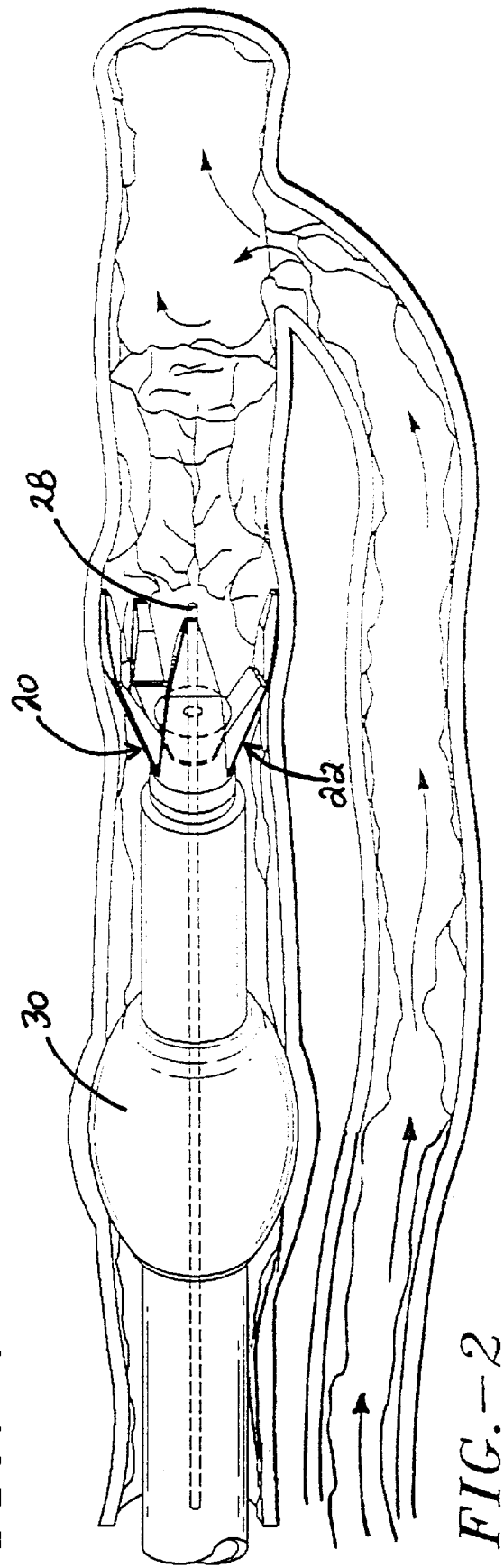

CATHETER SYSTEM FOR TREATING A VASCULAR OCCLUSION

BACKGROUND OF THE INVENTION

1. Field of the Invention

This invention relates generally to medical devices and especially intravascular catheters designed to operate with respect to occlusions within a blood vessel. More particularly, this invention relates to intravascular catheters having the ability to fracture an occlusion sufficiently for allowing a guide wire to pass through the occlusion within the natural lumen of the blood vessel.

2. Background

Medical science has long sought effective treatments for disease conditions involving stenosis (narrowing or obstruction) of the lumen (interior passage of the artery) of an artery. This condition, known generally as an occlusion, is found in patients suffering from atherosclerosis (accumulation of fibrous, fatty or calcified tissue in the arteries). An occlusion can manifest itself in hypertension (high blood pressure), ischemia (deficiency of circulation), angina (chest pain), myocardial infarction (heart attack), stroke, or death. An occlusion may be partial or total, may be soft and pliable or hard and calcified, and may be found at a great variety of sites in the arterial system including the aorta, the coronary and carotid arteries, and peripheral arteries.

Of particular interest to cardiac medicine are the often disabling or fatal occlusions occurring in the coronary arteries (arteries supplying the heart). Traditionally, coronary artery occlusions have been treated by performing coronary bypass surgery, in which a segment of the patient's saphenous vein is taken from the patient's leg and is grafted onto the affected artery at points proximal (upstream) and distal (downstream) to the occluded segment. The bypass often provides dramatic relief. However, it entails dangerous open chest surgery and a long, painful, costly convalescence in the hospital. Moreover, with the passage of time, the bypass patient's saphenous vein graft can also become occluded. If the patient has another saphenous vein, a second bypass procedure may be performed, once again entailing open chest surgery and prolonged hospitalization. Thereafter, if the underlying atherosclerotic disease process is not controlled, the prognosis is dismal.

Newer, minimally invasive procedures are now preferred in the treatment of arterial occlusions. These procedures use a catheter, a long, thin, highly flexible device which is introduced into a major artery through a small arterial puncture made in the groin, upper arm, or neck and is advanced and steered into the site of the stenosis. At the distal end of the catheter, a great variety of miniature devices have been developed for operating upon the stenosed artery.

The more popular minimally invasive procedures include percutaneous transluminal coronary angioplasty (PTCA), directional coronary atherectomy (DCA), and stenting. PTCA employs a balloon to mechanically dilate the stenosis. In PTCA, a steerable guidewire is introduced and advanced under fluoroscopic observation into the stenosed artery and past the stenosis. Next, a balloon-tipped catheter is advanced over the guidewire until it is positioned across the stenosed segment. The balloon is then inflated, separating or fracturing the atheroma (stenosed tissue). The hoped-for outcome is that, over time, the lumen will stay open.

In directional coronary atherectomy, a catheter containing a cutter housed in its distal end is advanced over the guidewire into the stenosed segment. The housing is urged against the atheroma by the inflation of a balloon, so that part of the atheroma intrudes through a window in the side of the housing. Under fluoroscopic observation, the cutter is used to shave away the atheroma. The shavings are collected in the nosecone of the housing and withdrawn along with the catheter.

Stenting is a procedure in which a wire framework, known as a stent, is compressed and delivered a balloon catheter. The stent is positioned across the stenosed segment of the artery. The balloon is inflated, dilating the stent and forcing the stent against the artery wall. The hoped-for outcome is that the stent will hold the arterial lumen open for a prolonged period. Frequently, a stent is placed in an artery immediately following PTCA or DCA.

It must be noted, however, that the aforementioned catheters are "over-the-wire catheters." These catheters depend on the guidewire, which typically has a tiny bent portion at its distal end for steering. Over-the-wire catheters cannot be positioned adjacent the stenosis until the guidewire has been advanced across the stenosed arterial segment. Thus, where the occlusion is too severe to be crossed by a guidewire or where there is not enough room for the balloon, cutter, or stent delivery catheter, neither PTCA nor DCA nor stenting can be done. Unfortunately, the occlusion often contains extremely hard, calcified tissue and presents an impenetrable barrier to the guidewire. Even a less than total occlusion may contain complex structures which divert or trap the steering end of the guidewire. Thus, the guidewire might not completely cross the occlusion, but become diverted into the subintimal space between the intima and the atheroma or become buried in the atheroma. In either case, the guidewire cannot be positioned across the stenosis to guide a balloon or cutting element. In such cases, bypass surgery may be necessary with the associated cost, risks, and recovery period.

Thus, in patients suffering from severe or total arterial occlusion, it is preferable to do what has been difficult or impossible in the past: to open the severely or totally occluded artery itself, rather than by performing a bypass. If a guidewire and working catheter can be passed through or around the atheroma, the severe or total occlusion can be treated by PTCA, DCA, stenting, site-specific drug delivery or a combination of these proven therapies.

It would be advantageous to find and open a path of low resistance, either through or around the atheroma. Of course, this must be done without perforating arterial wall. Clearly, the serious consequences of penetrating the arterial wall must be avoided at all costs. The physician will not use a system which would be unsafe and no patient would want a physician to use such a system. Therefore, any solution to the problem of finding and creating an opening through or around the atheroma must be safe and in many instances include a system of guidance for the device that would find and open such an occlusion.

There has been a long felt need to provide a reliable system of guidance for such a device. As understood by those in the art, the device must travel a crisscrossing, often maze-like structure before it even gets to the occlusion. Then the occlusion itself is often a maze like structure. Attempting to cross such an occlusion without reliable guidance is dangerous. For example, it is easy to dissect the tissues of the arterial wall instead of the occlusion, thereby creating a false lumen and possibly perforating the artery. If blood escapes the artery and accumulates in the pericardial space, it will compress the heart, requiring emergency intervention to avert heart failure and death.

One guidance system which has been used in conjunction with coronary catheterization is biplane fluoroscopy, wherein the interventionist observes two flat real-time x-ray images acquired from different angles. Biplane fluoroscopy, however, is unreliable, costly, and slow. Delay is unacceptable, for it contributes to trauma and stress and creates opportunities for complications and failures of technique.

Recently, promising optical systems have been disclosed for imaging an occlusion through a catheter placed in the artery. One such system is Optical Coherence Tomography (OCT). In OCT, a beam of light carried by an optical fiber illuminates the artery interior. In a radar-like manner, light reflected back into the fiber from features inside the artery is correlated with the emitted light to capture the depth as well as the angular separation of those features. The features are displayed graphically in two or three dimensions through the use of a suitably programmed computer.

The beam in OCT is swept by mechanical rotation or movement of optical components in the catheter, or by optical switching devices which select one of several fibers through which to perform measurements. The rotation is encoded, or the switching pattern recorded, for reconstructing angular information about the artery interior. For example, a beam splitter may be placed between the light source and the catheter fiber to produce a reference beam which is directed to a reflector at a known distance. The catheter beam and the reference beam are recombined as they return. When the paths traveled by the two beams are of equal optical length, interference fringes are observable in the combined beam. Since the lengths of the reference path and the catheter fiber are known, the distance from the fiber end to a particular reflective feature within the artery can be inferred. In OCT and related methods, signals may also be impressed upon the light beam to facilitate the measurement of distance or the detection of motion of objects relative to the fiber end. By means of OCT or other similar optical methods, imaging capability can be incorporated into an intravascular catheter or guidewire.

However, while superior imagery alone is of diagnostic interest, effective intervention for severe occlusive arterial disease is what is truly desired. Even with improved guidance, there persists a long felt need for working elements which are capable of opening a path through or around an arterial occlusion at low risk of perforating the artery. What is needed is an intravascular catheter system for the effective treatment of the severely occluded artery and, in particular, the totally occluded artery. What is especially needed is a therapeutic working element which allows the physician to mechanically fracture an occlusion or to separate the occlusion from the intimal surface, but which is operable in a manner unlikely to perforate the adventitia.

SUMMARY OF THE INVENTION

It is an object of this invention to provide a blunt end assembly for fracturing an occlusion within a blood vessel.

It is an additional object of this invention to provide such an assembly wherein the assembly includes a catheter having a distal end and a proximal end and wherein a working end member fits in an interchangeable manner to the distal end of the catheter and wherein the working end comprises a blunt end member in accordance with the invention.

It is an additional object of this invention to provide such an assembly wherein the blunt end member has a first closed position and a second open position and may be repeatedly opened and closed for fracturing the occlusion within the native lumen of the blood vessel.

In accordance with the above objects and those that will be mentioned and will become apparent below, the blunt end member assembly in accordance with this invention comprises:

a blunt end member connectable to the distal end of the catheter, the blunt end member sized and shaped for fitting within the blood vessel and for fracturing the occlusion, the blunt end member having a first position for allowing the blunt end member to be located at the occlusion and a second position for fracturing the occlusion; and an actuation member for moving the blunt end member between the first and second positions, whereby the blunt end member is connectable to the distal end of the catheter and the blunt end member is deliverable to the occlusion in the first position and is actuable to a second position for fracturing the occlusion.

In one exemplary embodiment of the invention, an over-the-wire intravascular catheter is provided comprising a blunt end member disposed at the distal end thereof and a securing balloon disposed about the distal end zone of the catheter proximal to the blunt end member. The catheter and blunt end member are sized and shaped so as to allow the blunt end member to be advanced into contact with an occlusion in an artery. The balloon is disposed on the outer surface of the distal end zone of the catheter and is inflatable to secure the distal end of the catheter within the artery and thus to maintain engagement of the blunt end member with the occlusion. A balloon inflation lumen is provided in the catheter.

The blunt end member comprises four jaw sections flexibly attached to the distal end of the catheter and arranged symmetrically about the longitudinal axis thereof. The catheter comprises a retractable actuation shaft having a ball-shaped ferrule fixed to the distal end thereof between the jaw sections. To accommodate a guidewire, the actuation shaft includes a lumen and the ferrule includes a center opening. The jaw sections have a first, closed position in which the catheter may be advanced to engage the jaws with the occlusion. When the actuation shaft is retracted, the ferrule impinges upon the inner surfaces of the jaw sections, urging them apart toward a second, open position to fracture the occlusion.

It is an advantage of this exemplary embodiment of the invention that fracturing force is stably applicable to a severe or total arterial occlusion. It is a further advantage of this exemplary embodiment that a mechanical working element is stably operable upon a severe or total arterial occlusion in a manner unlikely to perforate the adventitia.

In another exemplary embodiment of the invention, the jaw sections are spade-shaped. In the first, closed position, the jaw sections form a channel substantially confining the guidewire to the longitudinal axis of the blunt end member. It is an advantage of this exemplary embodiment that when the jaw sections are in the first, closed position, a guidewire may be advanced into a portion of the occlusion bounded by the points of contact with the distal ends of the jaw sections.

In another exemplary embodiment of the invention, the ferrule has a frusto-conical profile.

In another exemplary embodiment of the invention, each jaw section includes a rectangular distal end.

In another exemplary embodiment of the invention, the actuation member includes an actuation cable disposed in the catheter. The proximal end of the cable is manipulable from the proximal end of the catheter and the distal end of the cable is attached to the ferrule. It is an advantage of this exemplary embodiment of the invention that the cable increases the tension capacity of the actuation member during retraction of the ferrule.

In another exemplary embodiment of the invention, the jaw sections are fabricated from an alloy comprising Nickel and Titanium. It is an advantage of this exemplary embodiment of the invention that the superelastic properties of the alloy facilitate spreading of the jaw sections when the ferrule is retracted.

In another exemplary embodiment of the invention, a part of the lumen of the actuating member includes a friction reducing coating. It is an advantage of this exemplary embodiment of the invention that the catheter and blunt end slide easily over the guidewire.

In another exemplary embodiment of the invention, the mating surface defined by the impingement of the actuation member upon the blunt end member includes a friction reducing coating. It is an advantage of this exemplary embodiment of the invention that the actuation member encounters minimal frictional resistance while urging the jaw sections apart.

In another exemplary embodiment of the invention, the entire blunt end member is fabricated from a single piece of material. It is an advantage of this exemplary embodiment of the invention that fabrication of the blunt end member does not require attachment or assembly of multiple parts.

In another exemplary embodiment of the invention, the blunt end member includes a rigid tubular reinforcing member slidably disposed about the actuation shaft inside the distal end zone of the catheter. A tubular support member is disposed on the outer surface of the distal end of the catheter. The distal end of the support member includes a spring member deformably supporting a plurality of jaw sections. The support member is crimped onto the distal end zone of the catheter, securing the catheter onto the reinforcing member. It is an advantage of this exemplary embodiment of the invention that a simple yet secure attachment is formed between the catheter and the blunt end member.

BRIEF DESCRIPTION OF THE DRAWINGS

For a further understanding of the objects and advantages of the present invention, reference should be had to the following detailed description, taken in conjunction with the accompanying drawings, in which like parts are given like reference numerals and wherein:

FIG. 1 illustrates an exemplary embodiment of the blunt end member for fracturing a total occlusion in accordance with this invention shown in partial cross section.

FIG. 2 is a partial cross sectional view of the catheter having the blunt end member of FIG. 1 in the process of fracturing the total occlusion.

DETAILED DESCRIPTION OF THE INVENTION

Figures 3, 4:
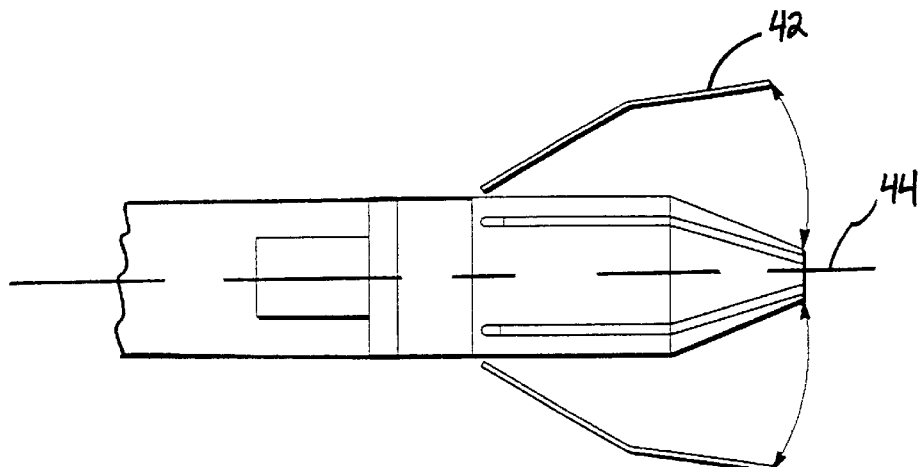
FIG. 3 is an enlarged side view of the blunt end member having a first closed position and a second open position.
FIG. 4 is an end view of the blunt end member of FIG. 3 in the first or closed position.

The invention will be described particularly with reference to a coronary bypass arterial condition. As illustrated in FIGS. 1 and 2, the blunt end member, in accordance with this invention, is shown adjacent to a total occlusion where a bypass is in the process of failing. The bypass has developed diffuse stenosis as shown in FIGS. 1 and 2. Consistent with the above description, it is quite likely that where stenosis has developed sufficiently to block an arterial blood vessel, after a bypass is performed, stenosis in the bypass will also accumulate. Even, to the point that the bypass may also be blocked or become totally occluded. Using the blunt end member, in accordance with this invention, the original, native blood vessel is reopened allowing the bypass to fade as the primary source of blood flow.

It will of course be appreciated that the drawings are illustrative only, and that the invention made be used in any situation where the blood vessel, such as a coronary artery has been occluded, by stenosis or other arterial disease. The principal feature of the invention is to fracture the stenosis occluding blood flow and allow the native artery to resume the primary responsibility for blood flow.

With particular reference to FIG. 1, there is shown the blunt end member assembly in accordance with this invention, generally designated by the numeral 20. The assembly 20 includes a blunt end member, generally indicated by the numeral 22, and a catheter 24. An actuation member indicated by doted lines 26 moves the blunt end member from a first closed position as illustrated in FIG. 1 to an second open position as illustrated in FIG. 2.

The catheter is positioned using a guide wire 28 as best shown in FIG. 2, so that the extreme distal end of the blunt end member is adjacent to the total occlusion, as shown in FIGS. 1 and 2. Once positioned, the catheter which includes, in a exemplary embodiment, a member for stabilizing the assembly 20 in the blood, namely, a balloon member 30. The balloon member 30 is inflated as shown in FIG. 2, so that the catheter remains in place during actuation of the blunt end member 22.

With particular reference to FIGS. 3 through 6, there is shown an exemplary first embodiment of the blunt end member 22. The blunt end member 22 has a proximal end 40 attached to the distal end of the catheter 24. The method of attachment is conventional within the skill and knowledge of the prior art and is not explained herein in detail.

Figure 5:
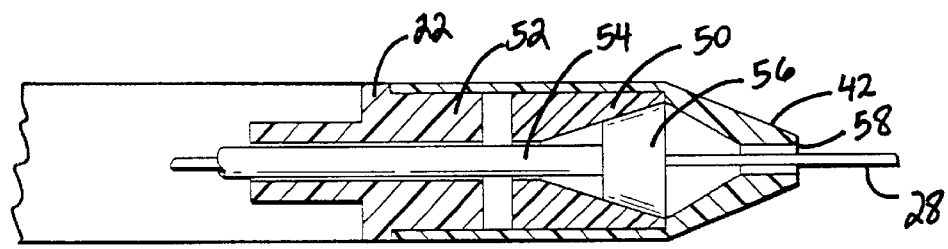
FIG. 5 is a cross sectional plane view of the blunt end member of FIG. 1 shown in cross sectional view.

The blunt end member includes a set of sectional members defining jaw sections 42. The jaw sections 42 are located at the distal end of the blunt end member and are spaced equal distance of the longitudinal center line 44. Thus, as will be appreciated herein after, the jaw sections 42 open to a second position shown particularly in FIGS. 3 and 6, and close to a first position as shown in FIGS. 3, 4, and 5. As will be explained below, an actuation member is required to move the jaw sections 42 from its first closed position to its second open position.

The jaw sections 42 are generally spade shaped and are separate from one another as illustrated. This allows the jaw sections to meet flush against the arterial wall and the occlusion for optimizing fracturing of the occlusion. The jaw sections 42 are spaced apart as shown in FIG. 4.

Figure 6:
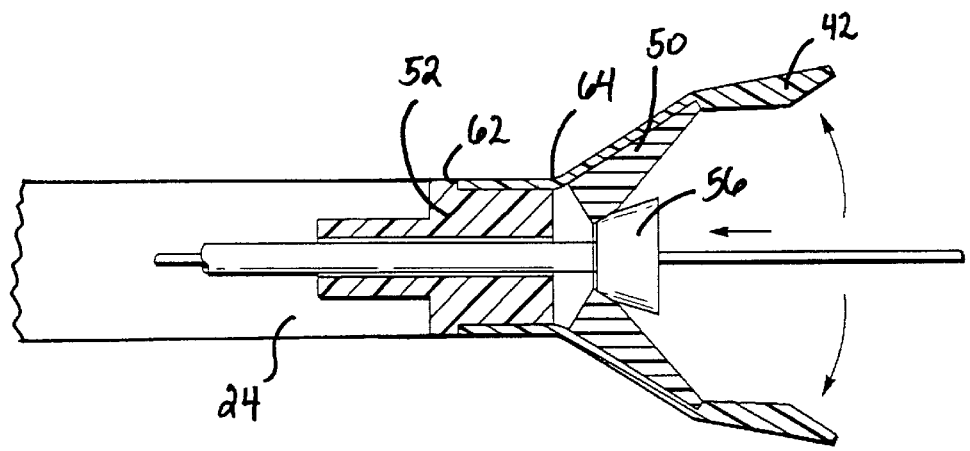
FIG. 6 is a cross sectional view of the blunt end member of FIG. 1 shown in the second open position.

With respect to FIGS. 5 and 6, there is shown an assembly view of the blunt end member 22 in accordance with the invention as illustrated in FIG. 4. FIG. 5 is a cross sectional view along line 5—5 of FIG. 4 and looking in the direction of the arrows. The blunt end member 22 includes a reverse conical urging member 50 and a spaced apart support member 52. The members 50 and 52 are sized and shaped to fit within the same cavity or lumen of the catheter 24.

Each of the members 50 and 52 includes a center opening along the longitudinal center line 44. The openings 50 and 52 are aligned so that a guide wire tube 54 is able to slide toward and away from the proximal end of the catheter 24.

Attached to the guide wire tube 54 is a ferrule 56. The ferrule 56 also has a center opening aligned with the center openings of the members of 50 and 52. However, the center opening of the ferrule 56 has a smaller diameter to match the guide wire 28 and not the guide wire tube 54. Thus, the ferrule 56 is designed to accommodate only the guide wire 28 and not the guide wire tube 54.

The guide wire 28 is shown inserted in the center opening of the ferrule 56. It will also be appreciated that the jaw sections 42 are spaced apart a sufficient distance along the longitudinal center line 44 so that the guide wire is guided thereby. As clearly shown in FIG. 5, the jaw sections 42, when closed, form a internal guide 58 for sliding the guide wire toward and away from the distal end of the catheter 24.

The ferrule 56 may be made from a variety of materials including stainless steel, nickel titanium or other shape memory alloys and various engineering plastics. Additionally, other polymers or metal materials, which are bio-compatible and have the mechanical characteristics necessary to perform the functions herein are equally suitable.

The ferrule defines a frusto-conical shape, while the urging member 50 forms a reverse compatible shape for sliding against the frusto conical shape of the ferrule 56. The surfaces where each of the ferrule 56 and the urging member 50 contact, define a mating surface. The materials selected for each of the ferrule 56 and urging member 50 are compatible for such mating sliding contact.

In response to actuation, the ferrule 56 is pulled toward the proximal end of the catheter 24 causing the ferrule 56 to slide against the urging member 50, the mating surfaces of each sliding across one another. As the ferrule is pulled towards the proximal end of the catheter, an increasing force is urged against the jaw sections 42 for spreading apart said jaw sections 42. Upon full activation of the actuation member the jaws are fully open, as shown in FIG. 6.

In an exemplary embodiment of the invention, the blunt end jaw members 42 must be made of material having sufficient strength to withstand the mechanical forces necessary to fracture the occlusion shown in FIGS. 1 and 2. In a preferred exemplary embodiment, the jaw sections are made from nickel titanium which has proven bio-compatible as well as having sufficient strength for the function intended herein.

The guide wire tube 54 is bonded to the ferrule as shown in FIGS. 5 and 6. The bonding may be similar to the bonding of the catheter and the blunt end member 22. Additionally, bonding may be done by use of adhesives such as loc-tite™, soldering, or chemical or physical bonding, of a suitable kind. The guide wire tube 54 being thus, permanently connected to the ferrule in a bond which is strong enough to withstand the urging forces exerted against the occlusion. The interior opening of the members 50 and 52, provides a guide for the guide wire tube 54 as the jaw sections 42 are opened and closed in repeated use. It may be advantages to coat the interior opening of the members 50 and 52, as well as the exterior of the guide wire 54, with Teflon or similar polymers so that the friction from the movement of sliding through the internal opening is greatly reduced. A reduction in friction will, of course, result in more force being applied by the ferrule 56 against the urging member 50 to maximize the amount of fracturing power generated by the blunt end member 42.

Conventionally, the guide wire tube 54 is a braided strand, and thus can be quite abrasive to the internal opening of the members of 50 and 52. Thus, the matter of applying a coating may be increasingly important to reduce the friction in the sliding movement. Additionally, it is preferable that the mating surfaces of the urging member 50 and the ferrule 56 also be as smooth as possible and chosen from compatible materials to minimize the amount of friction developed as the mating surfaces slide against one another in an effort to fracture the occlusion of FIGS. 1 and 2. In an exemplary embodiment the ferrule and urging members are both made from nickel titanium. In another embodiment, the urging member 50 is made from stainless steel and the ferrule 56 is made from nickel titanium. Again, the mating surfaces of the ferrule 56 and urging member 50 are made as smooth as possible to minimize the friction there between.

As will be appreciated, the support member 52 provides support both internal and external to the assembly 20. The support member 52 remains fixedly attached to the distal end of the catheter 24 and provides an internal opening for the sliding movement of the guide wire tube 54. Additionally, as will be appreciated in FIGS. 5 and 6, the jaw sections 42 have a proximal end zone 60 which surrounds both the urging member 50 and the support member 52. The proximal end zone of the jaw sections 42 secures the members 50 and 52 together to provide the assembly 20. As shown in FIG. 6 the support member is notched at shoulder 62 to provide a secure connection fit with the jaw sections 42.

It will, of course, be appreciated that the entire assembly, including members 50 and 52, as well as jaw sections 42, may be made from a single piece of nickel titanium (NiTi) for a unified assembly. In another exemplary embodiment in accordance with a unified assembly, the jaw sections would be notched with an opening at elbow 64, as shown in FIG. 6. This would allow space for deformation of the jaw sections along an axis predetermined by the angle and length of the opening.

Figure 7:
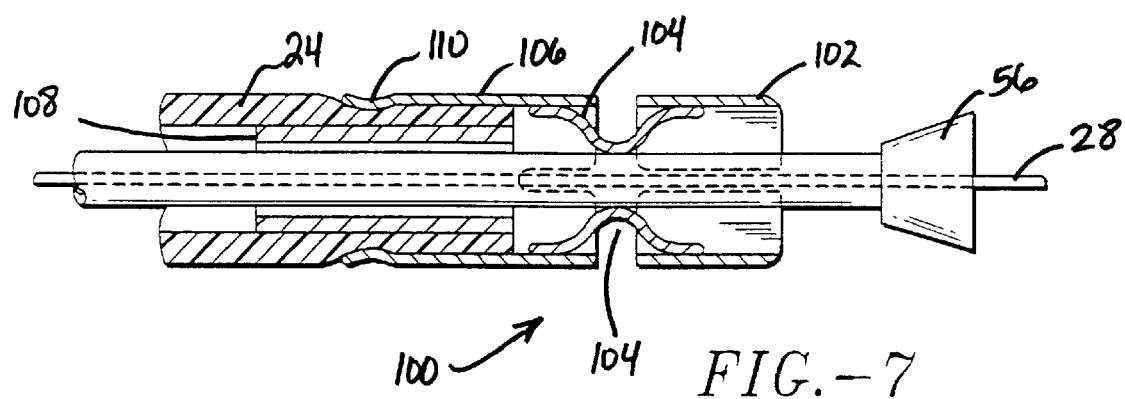
FIG. 7 is a cross sectional plane view of another exemplary embodiment of the blunt end member in accordance with this invention.
Figure 8:
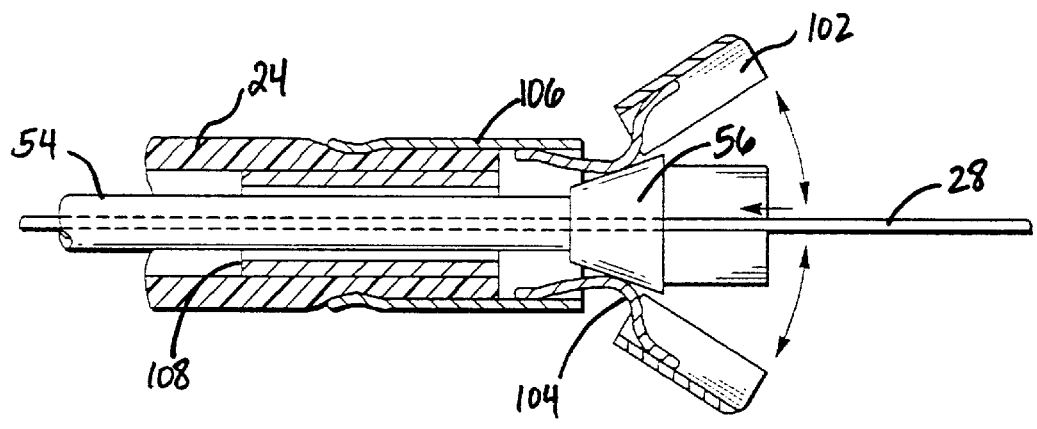
FIG. 8 is a cross sectional view of the blunt end member of FIG. 7 shown in the second open position.
Figure 9:
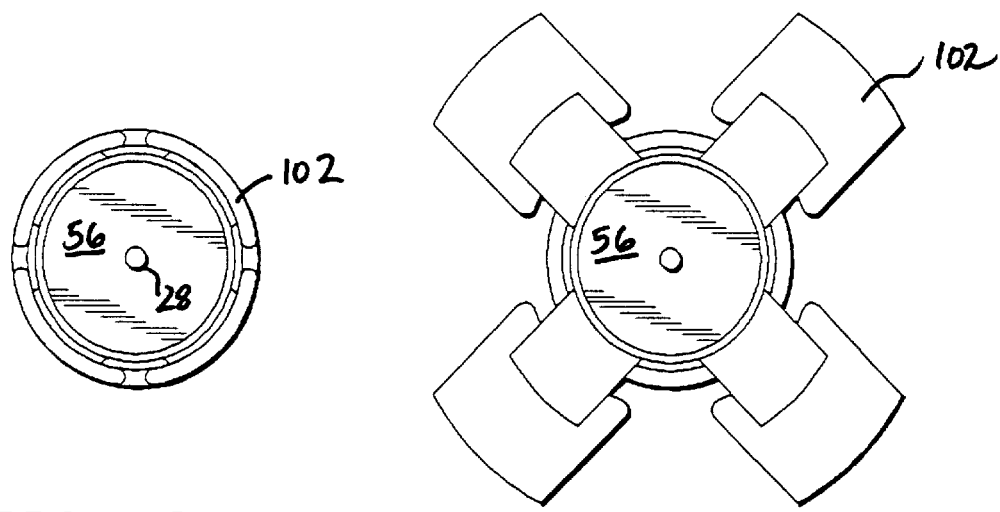
FIG. 9 is an end view of the blunt end member of FIG. 8.
Figure 10:
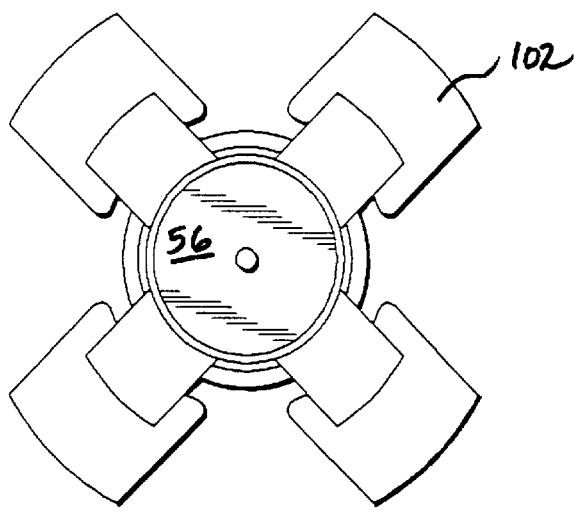
FIG. 10 is an enlarged end view of the blunt end member of FIG. 7 shown in the second or open position.

With respect to FIGS. 7 through 10, there is shown a second embodiment of the blunt end member in accordance with this invention, generally designated by the numeral 100. The blunt end member 100 includes jaw sections, as illustrated in FIGS. 8 and 10, designated by the numeral 102. The blunt end member 100 includes a spring member 104 and a support member 106. A reinforcing member 108 is positioned between the catheter tube 24 and the guide wire tube 54 in the guide wire lumen of the catheter tube 24. Attached to the guide wire tube 54 is a ferrule 56 as discussed previously with regard to the earlier described embodiment.

Similar to the reverse conical urging member 50, the spring member 104 has a mating surface for mating with the ferrule 56, as clearly shown in FIG. 8. Upon actuation, the ferrule 56 is pulled toward the proximal end of the catheter 24 and the mating surfaces engage and separate the jaw sections 102, as shown in FIGS. 8 and 10. Upon releasing the actuation member, the spring member 104 urges the jaw sections 102, back to their original and first closed positioned, as clearly shown in FIGS. 7 and 9. The spring member 104 serves to connect the jaw sections 102 and the rest of the blunt end member 100, and specifically the support member 106. The support member 106 is crimped at its proximal end 110. The reinforcing member 108 is positioned so that the crimp in the support member 106 sandwiches the distal end of the catheter tube 24. It will be appreciated that the hoop strength provided by the reinforcing member 108 enables a secure attachment of the support member to the distal end of the catheter tube 24. It will be further appreciated that the crimp in the support member, plus the added hoop strength provided by the reinforcing member 108, provide a secure connection for the entire blunt end member 100.

Typically the blunt end member is supported by the connections at the joining of the spring 104, the jaw sections 102, and support member 106. These joints can be done in a variety of ways. For example, it is preferable to bond the members with an epoxy, should they be made of a polymer or to use welding, soldering, or brazing, if the members are made from metal.

In a preferred exemplary embodiment, the spring 104 is made from nickel titanium as are the support member 106 and jaw sections 102. In other embodiments, it is contemplated within the scope of this invention to make the support and spring members, 106 and 104, respectively, from stainless steel. Additionally, the reinforcing member 108 may be made alternately from nickel titanium or stainless steel. It is also contemplated that various other types of materials are suitable for manufacturing of the blunt end member 100 as described above.

The operation of the second exemplary embodiment will now be described in detail with reference to FIGS. 7 through 10. As shown in FIG. 7, the blunt end member 100 is in its normal or first closed position, as clearly illustrated in FIG. 7. As is typical in DCA operations, the guide wire 28 is fed through the lumen of the blood vessels of a patient. Upon reaching the selected location, such as that illustrated in FIGS. 1 and 2, the guide wire will meet an occlusion. The blunt end member 100 with ferrule 56 will be positioned, as described earlier, directly adjacent to the occlusion. Although not shown, it will be appreciated that the balloon 30 of FIGS. 1 and 2 may also be adapted for use with the second exemplary embodiment shown in FIGS. 7 through 10.

After stabilization of the catheter 24 in the lumen of the blood vessel, the blunt end member 100 is activated by pulling on an actuation member such that the mating surfaces of the spring 104 and the ferrule 56 are brought into contact with one another. The ferrule 56 moves the jaw sections 102 away from the longitudinal center line 44 of the catheter as described earlier with reference to FIGS. 1 through 6. This operation is repeated until fracturing occurs, as clearly shown in FIG. 2. Once fracturing occurs, and the guide wire 28 can be fed through the natural lumen of the blood vessel, the catheter may be removed and another working end may be brought to bear upon the occlusion. Such working end may include an angioplasty device, atherectomy catheter device, or a stent or other known medical methods, for removing the occlusion once the guide wire 28 is across the occlusion.

While the foregoing detailed description has described several embodiments of the method in accordance with this invention, it is to be understood that the above description is illustrative only and not limiting of the disclosed invention. Particularly, the invention need not be limited to a ferrule having a frusto-conical shape. It will be appreciated that a spherical ferrule could also be used within the spirit and scope of this invention. It will also be appreciated that the various elements which make up the blunt end member may be made from stainless steel, or some engineering plastic, including a suitable polymer. Additionally, while the invention has been described with regard to a bypass type of operation, it will be appreciated that other medical procedures wherein a occlusion blocks a blood vessel, or substantially blocks a blood vessel, or at least prevents a guide wire from easy going across the occlusion, are suitable for use with the invention described herein. Thus, the invention is to be limited only by the claims as set forth below.

What is claimed is:

1. An assembly for a catheter having a proximal end and a distal end and longitudinal axis between the ends, the assembly designed for fracturing an occlusion within a blood vessel, the assembly comprising:

a blunt end member connectable to the distal end of the catheter, the blunt end member sized and shaped for fitting within the blood vessel and for fracturing the occlusion, the blunt end member having a first position for allowing the blunt end member to be located at the occlusion and a second position for fracturing the occlusion; and an actuation member for moving the blunt end member between the first and second positions, whereby the blunt end member is connectable to the distal end of the catheter and the blunt end member is deliverable to the occlusion in the first position and is actuable to a second position for fracturing the occlusion wherein the actuation member comprises:

an actuation shaft extending from the blunt end member to the proximal end of the catheter; and a ferrule, fixed to the distal end of the actuation shaft, impinging upon the blunt end member, whereby, upon actuation, the shaft is pulled toward the proximal end, urging the blunt end member to a second position.

2. The assembly as set forth in claim 1 wherein the catheter includes a selectively activatable securing member for holding the catheter in place at the location of the occlusion.

3. The assembly as set forth in claim 2 wherein the securing member comprises an inflatable balloon disposed about the outer surface of the catheter proximate the blunt end member and the catheter includes at least one balloon inflation lumen communicating with the interior of the balloon.

4. The assembly as set forth in claim 1 wherein the catheter includes a securing member for holding the catheter in place at the location of the occlusion; the securing member being selectively activatable.

5. The assembly as set forth in claim 1, wherein the catheter has multiple lumens, at least one lumen for actuation shaft.

6. The assembly as set forth in claim 1, wherein the blunt end member includes a plurality of jaw sections disposed about the longitudinal axis of the catheter, the jaw sections having a first position wherein the jaw sections are closed for location adjacent the occlusion and a second position wherein the jaws are open for fracturing the occlusion.

7. The assembly as set forth in claim 6 further comprising a guidewire disposed in the catheter, wherein the jaw sections are so shaped that, in at least one position, the jaw sections form a channel substantially confining the guidewire to the longitudinal axis of the assembly.

8. The assembly as set forth in claim 6, wherein the jaw sections are fabricated from an alloy comprising Nickel and Titanium.

9. The assembly as set forth in claim 6, wherein the ferrule includes a longitudinal center opening for accommodating a guidewire.

10. The assembly as set forth in claim 6, wherein the blunt end member is fabricated from a single piece of material.

11. The assembly as set forth in claim 1, wherein at least a part of the lumen of the actuating member includes a friction reducing coating.

12. The assembly as set forth in claim 1, wherein the actuation member slides against the blunt end member along a region that defines at least one mating surface and wherein the mating surface includes a friction reducing coating.

13. The assembly as set forth in claim 1, wherein the blunt end member further comprises:
   a rigid tubular reinforcing member fixed within the distal end zone of the catheter and slidably disposed about the actuation shaft;
   a tubular support member including a proximal end fixedly disposed on the outer surface of the distal end of the catheter and further including a distal end; and
   a spring member including a proximal end connected to the distal end of the support member and a distal end deformably supporting a plurality of jaw sections.

14. The assembly as set forth in claim 13, wherein the support member is crimped onto the distal end zone of the catheter.

15. The assembly as set forth in claim 1, wherein the catheter has multiple lumens, at least one lumen for the securing member.

16. The assembly as set forth in claim 1, wherein the actuating member includes an outer surface and at least a part of the outer surface of the actuating member includes a friction reducing coating.

17. A catheter assembly for crossing a vascular occlusion comprising:
   a catheter having a proximal end and a distal end defined by a longitudinal axis extending between the proximal and distal ends of the catheter;
   at least one hinged jaw section sized and shaped for placement within a blood vessel that is formed with a deformably supportive elbow wherein the jaw section is positioned at the distal end portion of the catheter and is movable about the supportive elbow between an open position and a closed position to displace a vascular occlusion; and
   an actuation member positioned along a relative portion of the catheter for moving the at least one jaw section between its open and closed position.

18. The assembly as set forth in claim 17 wherein at least one jaw section is spade-shaped.

19. The assembly as set forth in claim 17 wherein at least one jaw section includes a distal end having a rectangular shape.

20. The assembly as set forth in claim 17 wherein at least one jaw section has a rectangular paw disposed at the distal end thereof.

21. The assembly as set forth in claim 17 wherein the actuation member comprises:
   an actuation shaft, disposed in the catheter, having a proximal end manipulable from the proximal end of the catheter and a distal end proximate the distal end of the catheter and proximate the jaw section, and
   a ferrule, attached to the distal end of the actuation shaft, disposed proximate the jaw section.

22. The assembly as set forth in claim 21 wherein the ferrule has a frusto-conical profile.

23. The assembly as set forth in claim 21 wherein the ferrule has a ball-shaped profile.

24. The assembly as set forth in claim 21 further comprising an actuation cable, disposed in the catheter, having a proximal end manipulable from the proximal end of the catheter and a distal end attached to the ferrule.

25. The assembly as set forth in claim 17 wherein the catheter includes a securing member for holding the catheter in place at the location of the occlusion; the securing member being selectively activatable.

26. The assembly as set forth in claim 17, wherein the actuating member includes a proximal end, a distal end, and a lumen therebetween for accommodating a guidewire.

27. The assembly as set forth in claim 26, wherein at least a part of the lumen of the actuating member includes a friction reducing coating.

* * * * *